(12) United States Patent
Sherif (10) Patent No.: US 8,372,145 B2
(45) Date of Patent: Feb. 12, 2013

(54) IMPLANTABLE ARTIFICIAL VENTRICLE HAVING LOW ENERGY REQUIREMENT

(76) Inventor: Hisham M. F. Sherif, Newark, DE (US)

( * ) Notice: Subject to any disclaimer, the term of this patent is extended or adjusted under 35 U.S.C. 154(b) by 686 days.

(21) Appl. No.: 12/549,561

(22) Filed: Aug. 28, 2009

(65) Prior Publication Data

US 2010/0298932 A1    Nov. 25, 2010

Related U.S. Application Data

(60) Provisional application No. 61/216,641, filed on May 19, 2009.

(51) Int. Cl.
*A61M 1/10* (2006.01)

(52) U.S. Cl. ...................................... 623/3.17; 623/3.11
(58) Field of Classification Search .................. None
See application file for complete search history.

(56) References Cited

U.S. PATENT DOCUMENTS

| | | | |
|---|---|---|---|
| 3,568,214 A | 3/1971 | Goldschmied | 3/1 |
| 4,621,617 A | 11/1986 | Sharma | 128/1 D |
| 4,731,076 A | 3/1988 | Noon et al. | 623/3 |
| 5,139,516 A | 8/1992 | Mogendovich | 623/3 |
| 5,268,082 A | 12/1993 | Oguro et al. | 204/282 |
| 5,456,715 A | 10/1995 | Liotta | 623/3 |
| 5,556,700 A | 9/1996 | Kaneto et al. | 428/322 |
| 5,630,709 A | 5/1997 | Bar-Cohen | 417/322 |
| 5,855,565 A | 1/1999 | Bar-Cohen | 604/104 |
| 5,947,892 A | 9/1999 | Benkowski et al. | 600/16 |
| 5,961,298 A | 10/1999 | Bar-Cohen et al. | 417/322 |
| 6,058,958 A | 5/2000 | Benkowski et al. | 137/14 |
| 6,183,412 B1 | 2/2001 | Benkowski et al. | 600/16 |
| 6,249,076 B1 | 6/2001 | Madden et al. | 310/363 |
| 6,394,997 B1 | 5/2002 | Lemelson | 604/890.1 |
| 6,664,718 B2 | 12/2003 | Pelrine et al. | 310/800 |
| 6,682,500 B2 | 1/2004 | Soltanpour et al. | 604/9 |
| 6,979,423 B2 | 12/2005 | Moll | 422/45 |
| 7,175,588 B2 | 2/2007 | Morello | 600/17 |
| 7,303,581 B2 | 12/2007 | Peralta | 623/3.27 |
| 7,353,747 B2 * | 4/2008 | Swayze et al. | 92/92 |
| 7,371,223 B2 * | 5/2008 | Couvillon et al. | 604/9 |
| 7,397,166 B1 | 7/2008 | Morgan et al. | 310/328 |
| 7,411,332 B2 | 8/2008 | Kornbluh et al. | 310/311 |
| RE40,669 E * | 3/2009 | Palmer | 600/16 |
| 7,537,197 B2 | 5/2009 | Heim et al. | 251/129.06 |
| 2004/0008853 A1* | 1/2004 | Pelrine et al. | 381/191 |
| 2004/0230090 A1* | 11/2004 | Hegde et al. | 600/18 |
| 2006/0036127 A1* | 2/2006 | Delgado, III | 600/16 |
| 2006/0217588 A1* | 9/2006 | Gross et al. | 600/16 |
| 2009/0156885 A1 | 6/2009 | Morello et al. | 600/16 |

OTHER PUBLICATIONS

Seigel-Itzkovich, "Israeli Surgeons Implant First Permanent Artificial Ventricle," 321 *Brit.Med.J.* 399 (2000).
Smulders et al., 15 *Artificial Organs* 96 (1991) (Abstract).
Yu et al., 35 *ASAIO Trans/Am.Soc.Artificial Internal Organs* 301 (1989) (Abstract).

(Continued)

*Primary Examiner* — Thomas J Sweet
*Assistant Examiner* — Rebecca Preston
(74) *Attorney, Agent, or Firm* — James C. Lydon (57) ABSTRACT

A pulsatile, positive-displacement mechanical circulatory support pump which can be used for assistance or replacement of one or both ventricles. The pump includes a plurality of contractile elements radiating outward from an apex of a compliance chamber, the elements being incorporated in and/or in contact with at least a portion of an outer surface of the compliance chamber. These contractile elements include an electroactive dielectric elastomer or an ion exchange membrane metallic composite. Application of electric field pulses from an implantable electrical energy source such as a pacemaker will cause the contractile elements to compress and expand the compliance chamber.

22 Claims, 6 Drawing Sheets

OTHER PUBLICATIONS

Chandran et al., 36 *ASAIO Trans./Am.Soc.Artificial Internal Organs* 132 (1989) (Abstract).
Ashley, *Scientific American* 53 (Oct. 2003).
Bar-Cohen, *Robotics 2000 and Space 2000* (2000).
Oguro, "Preparation Procedure Ion-Exchange Polymer Metal Composites (IPMC) Membranes," http://ndeaa.jpl.nasa.gov/nasa-nde/lommas/eap/IPMC_Prep-Procedure.htm.

* cited by examiner

IMPLANTABLE ARTIFICIAL VENTRICLE HAVING LOW ENERGY REQUIREMENT

This application claims the benefit of U.S. provisional application 61/216,641, filed May 19, 2009, whose disclosure is incorporated by reference herein in its entirety.

This invention relates to the field of cardiology. More particularly, this invention relates to an implantable ventricle assist device.

BACKGROUND OF THE INVENTION

Open heart surgery, such as a triple bypass or aortic artery repair, often requires stopping the patient's heart. A cardiopulmonary bypass machine ("heart-lung machine") comprising a pump and a membrane oxygenator is used to assist or replace normal heart function by circulating and oxygenating the patient's blood during the operation.

Heart-lung machines provide only very short-term (3-5 hours) cardiac function during surgery. However, many end-stage chronic heart failure patients require intermediate, long-term and even permanent cardiac assistance. For example, an artificial heart pump may be used to keep a patient alive while he is waiting for a donor organ to become available. Other patients may require cardiac assistance after cardiac surgery. The domestic demand for a simple, long-term ventricle assist device has been estimated at between 50,000 and 100,000 patients/year.

One of the first artificial ventricles was a pneumatically driven left ventricle, implanted in a patient in 1967. An air pump was located outside the patient's body, and a hose extended from the air pump to the implanted device.

There has been a demand ever since for a ventricular assist device which is completely implantable (without any protruding drive, vent or control cables), produces a pulsatile perfusion pattern, has a reliable long term power supply and a long service life, and is quiet. Unfortunately, known devices which seek to mimic native heart function suffer from high energy requirements, which in turn require external (extracorporeal) power sources.

The need for an extracorporeal power source requires an electrical cable to break the skin, which poses an increased risk of serious infection and, not incidentally, can be painful.

The high energy requirement of known devices means they have a short service life. Thus, patients must either change battery packs every few hours or remain within a short distance from a power outlet. The patient's mobility and quality of life are seriously comprised.

Piezoelectric motors which have relatively low power requirements, little heat dissipation and little noise generation have been suggested for heart assist devices. However, piezoelectric drive systems have also been unsuccessful because their output frequency, pressure and displacement are incompatible with those of the human heart.

In short, there is a long-felt but heretofore unsatisfied need for a totally implantable device which can provide long term cardiac assistance (pulsatile perfusion) without drastically reducing the patient's quality of life.

SUMMARY OF THE INVENTION

The invention relates to an artificial ventricle, comprising (A) a pulsatile, positive-displacement blood pump comprising a biologically inert housing containing a hollow, flexible compliance chamber,
at least one inlet valve for said compliance chamber, said inlet valve adapted to be operatively connected to a patient's ventricular apex or atrial wall,
at least one outlet valve for said compliance chamber, said outlet valve adapted to be operatively connected to the patient's aorta or pulmonary artery;
a plurality of contractile elements radiating outward from an apex of said compliance chamber, said elements being incorporated in and/or in contact with at least a portion of an outer surface of said compliance chamber, said contractile elements comprising an electroactive dielectric elastomer or an ion exchange membrane metallic composite, said contractile elements operatively connected to a common electrode, and (B) an implantable electrical energy source operatively connected to said common electrode,
wherein said electroactive dielectric elastomer is a member of the group consisting of polyaniline elastomers, polysulfone elastomers, polyacetylene elastomers, polypyrrole elastomers, polyvinylidene difluoride elastomers, silicone elastomers, and acrylic elastomers.

DETAILED DESCRIPTION OF THE PREFERRED EMBODIMENTS

The pulsatile, positive-displacement blood pump has a biologically inert housing, which may be made of any suitable material, with titanium and polyurethane being preferred. The pump's dimensions should permit the intake of an adequate volume of blood, yet be sufficiently small to permit implantation into the human body.

The housing contains a hollow, flexible compliance chamber whose internal volume is sufficient to permit pumping of an adequate amount of blood with each "beat" of the pump. For an adult, an internal volume of 20 to 80 cc is preferred. A compliance chamber intended for adult use may have a height of 4-10 cm and a diameter of 4-8 cm.

The artificial ventricle of the present invention may also be used for children. For pediatric use, an internal volume of 10 to 40 ml for the compliance chamber is preferred. A compliance chamber intended for pediatric use may have a length of 2-6 cm, a width of 2-3 cm and height of 2-3 cm.

The compliance chamber can be made of a blood-compatible, low thrombogenic material such as polyester or polytetrafluoroethylene. A preferred polyester material is polyethylene terephthalate coated with collagen.

The compliance chamber may be a woven or nonwoven fabric, such as knitted double velour fabric or woven double velour fabric. The interior surface of the compliance chamber should be as smooth as possible to minimize formation of blood clots. The exterior surface of the compliance chamber may be smooth or it may be ridged to facilitate placement of contractile elements (discussed below) and to minimize or eliminate slippage of contractile elements during artificial ventricle operation.

The compliance chamber is in fluid communication with at least one inlet valve and at least one outlet valve. The inlet valve is adapted to be operatively connected to a patient's ventricular apex or atrial wall, while the outlet valve is adapted to be operatively connected to the patient's aorta or pulmonary artery. In an preferred embodiment, the inlet valve comprises a cylindrical channel in communication with the compliance chamber, the channel containing a conventional one-way valve which can be a mechanical valve or a bioprosthetic valve. Illustrative mechanical valves include, without limitation, a ball check valve, a bi-leaflet valve and a tilting disc valve. Illustrative bioprosthetic valves include, without limitation, pericardial and porcine valves. In similar fashion, the outlet valve comprises a cylindrical channel in communication with the compliance chamber, the channel containing a one-way valve selected which can be a mechanical or bioprosthetic valve.

In one preferred embodiment, the inlet and outlet valves are located at a base of the ventricle housing, with the inlet and outlet valves arranged at an angle of 90 to 120° to one another.

The compliance chamber has a plurality of contractile elements which radiate outward from an apex of the compliance chamber. In a preferred embodiment, the contractile elements are in elongated or strip form and are helically arranged around the apex of the compliance chamber. Moreover, two or more of the contractile elements may be inter-connected at a point other than the apex.

The contractile elements comprise known electroactive dielectric elastomers or an ion exchange membrane metallic composites. Suitable dielectric elastomers include polyaniline elastomers, polysulfone elastomers, polyacetylene elastomers, polypyrrole elastomers, polyvinylidene difluoride elastomers, silicone elastomers, and acrylic elastomers. Acrylic elastomers are preferred.

Those of ordinary skill in the art can prepare electroactive dielectric elastomers using readily available materials and well-known techniques. See, for example, U.S. Pat. No. 7,537,197, the disclosure of which is incorporated by reference in its entirety herein.

Suitable ion exchange membrane metallic composites include perfluorocarboxylate-gold and sulfonated poly(styrene-ethylene-butylene-styrene). Those of ordinary skill in the art can prepare these composites using readily available materials and well-known techniques. See, for example, Oguro, "Preparation Procedure Ion-exchange Polymer Metal Composites (IPMC) Membranes," http://ndeaa.jpl.nasa.gov/nasa nde/lommas/eap/IPMC_PrepProcedure.htm, the disclosure of which is hereby incorporated by reference in its entirety.

The contractile elements are incorporated in and/or attached to at least a portion of an outer surface of the compliance chamber, and operatively connected to a common electrode. Their function is to sequentially expand and compress the compliance chamber, thereby inducing blood to enter and fill the chamber from the inlet valve, followed by ejection from the chamber through the outlet valve. These contractile elements deform (compress) the compliance chamber upon application of an electric field, and can be designed to exert a force of up to 34 mPa. More typically, these contractile elements can exert a force of about 5 Mpa, and exhibit a strain (amount of displacement or travel per unit length) of approximately 2%. This displacement can be achieved at a voltage of less than 10 volts, typically 2-4 volts.

Upon removal of the electric field, the contractile elements assume their original shape, thereby expanding the compliance chamber back to its original shape.

The compliance chamber may have additional contractile elements arranged circumferentially around its base to adjust the blood pump pulse.

The shape of the artificial ventricle is not critical, as long as it can fit within the human body. An adult version preferably is dome-shaped, with both the inlet and outlet valves located at the base of the housing, and arranged at an angle of 90 to 120° to one another. A pediatric version of the artificial ventricle is preferably in the shape of a somewhat curved cylinder, with the inlet and outlet valves at opposite ends of the cylinder.

The artificial ventricle includes an implantable electrical energy source operatively connected to the common electrode, preferably with a common voltage regulator operatively connected between the common electrode and the plurality of contractile elements. The implantable electrical energy source can be attached to or contained within the housing or, alternatively, the electrical energy source can be separate from the ventricle housing and connected thereto by an electrical cable. In a preferred embodiment, the electrical energy source is a modified pacemaker connected to the artificial ventricle by an electrical cable.

The housing of the artificial ventricle, and the housing of the implantable electrical energy source, should be impermeable to and sealed against body fluids. Accordingly, the openings in the artificial ventricle and the implantable electrical energy source for the electrical cable joining them should be sealed against ingress of such fluids.

The artificial ventricle is preferably operated by a drive circuit analogous to conventional implantable permanent pacemaker circuitry. More particularly, the drive circuit includes an electronic clock circuit and a pulse generator producing cyclic pulses having a biphasic square wave form. Illustrative circuit parameters are set forth below:

Voltage between 2 and 4 volts;
Amplitude of 2-5 mA;
Pulse duration of 20 msec;
Pulse frequency of 60 Hz (60 cycles/min., variable); and
Inter-pulse delay of 20 msec.

The contractile elements will deform in response to the automatic firing of the pacemaker pulse generator, compressing the compliance chamber and thus ejecting blood into the arterial side of the circulation. Preferably, the pacemaker circuitry will also be capable of automatic regulation of the artificial ventricle's pump rate depending on the patient's physiologic needs of the patient.

The electrical energy source which powers the drive circuit is preferably a durable, high capacity implantable energy source such as a lithium ion battery or other similar battery currently in use for implantable pacemakers and implantable cardioverters/defibrillators.

In a preferred embodiment, the electrical energy source and the drive circuit are housed in a hermetically sealed, impervious shell constructed of a biocompatible, inert material similar such as titanium or polyurethane.

The artificial ventricle may be implanted using conventional surgical techniques in which an inlet graft in communication with the inlet valve is connected to the ventricular apex or the atrial wall (systemic or pulmonary) and an outlet graft in communication with the outlet valve is anastomosed to the aorta or pulmonary artery, respectively. The common electrode is connected to the implantable electrical energy source, preferably a commercially available cardiac pacemaker, which is also implanted within the patient. Accordingly, the artificial ventricle is completely internalized, with no external components traversing the patient's skin.

Figure 1:
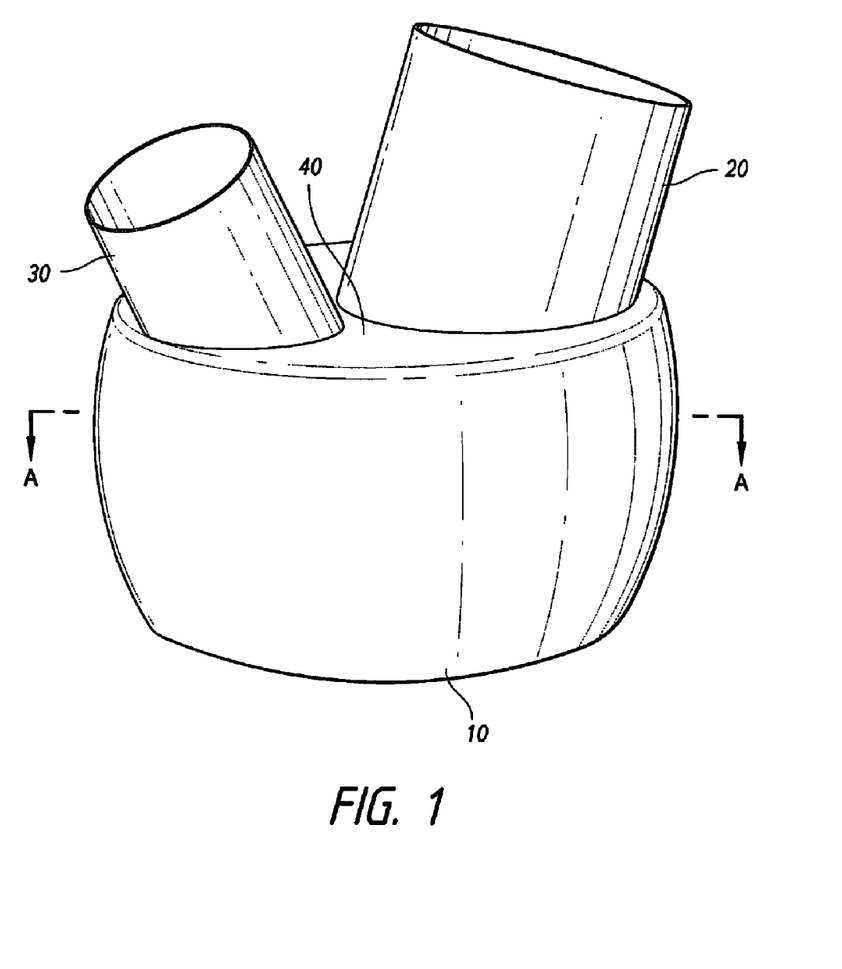
FIG. 1 is a plan view of an adult version of the artificial ventricle of the present invention.
Figure 2:
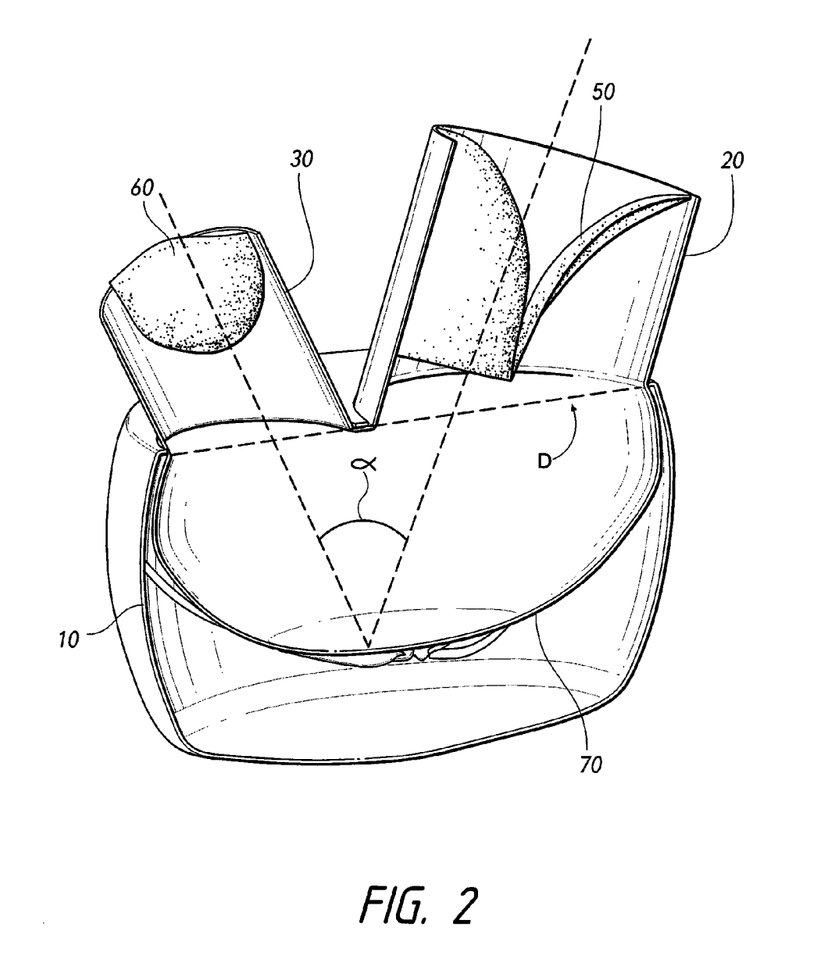
FIG. 2 is a cross-section of the artificial ventricle illustrated along plane A-A in FIG. 1.
Figure 3:
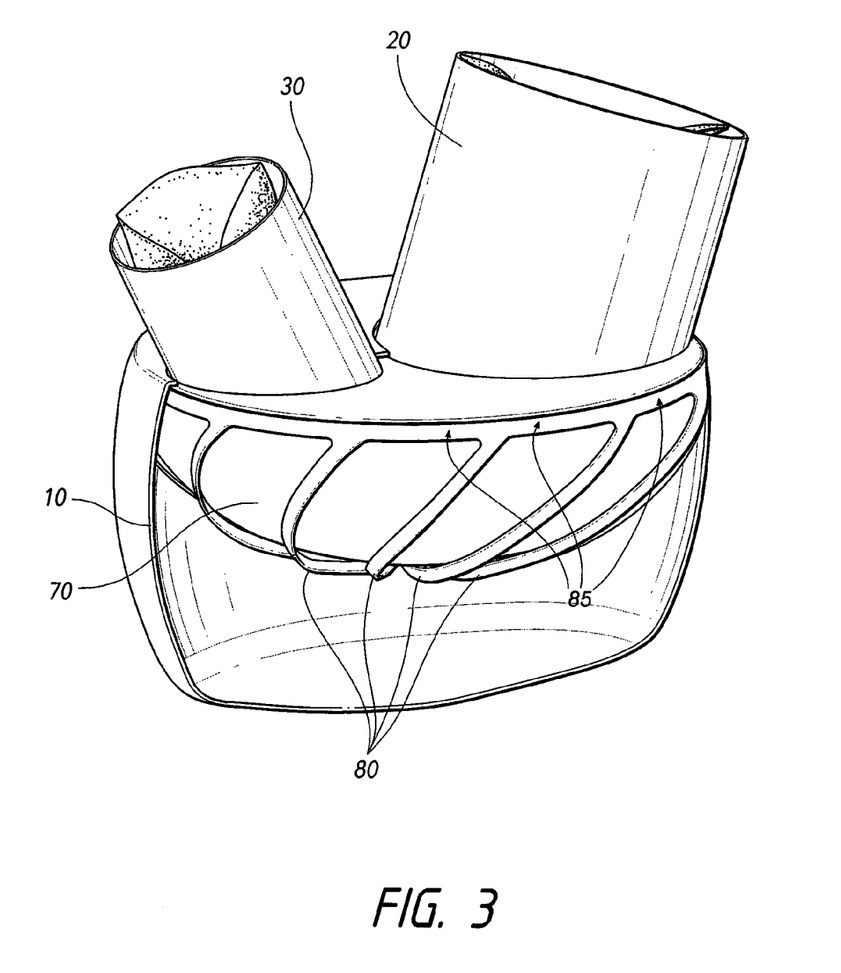
FIG. 3 is a partial plan view of the interior of the artificial ventricle of FIG. 1.

FIGS. 1-3 illustrate one embodiment of an adult version of the artificial ventricle of the present invention. Referring to FIG. 1, artificial ventricle housing 10 has a truncated dome shape with inlets 20 and 30 extending from base 40.

FIG. 2 is a cross section of the artificial ventricle illustrated along plane A-A in FIG. 1, and shows tri-leaflet pericardial valves 50 and 60 located within inlet 20 and outlet 30, respectively, which are both in communication with compliance chamber 70. Angle α between pericardial valves 50 and 60 may range from 90° to 120°.

FIG. 3 is a partial plan view of the interior of the artificial ventricle of FIG. 1, and shows helical contractile elements 80, and circumferential contractile elements 85, on the exterior surface of compliance chamber 70.

Figure 4:
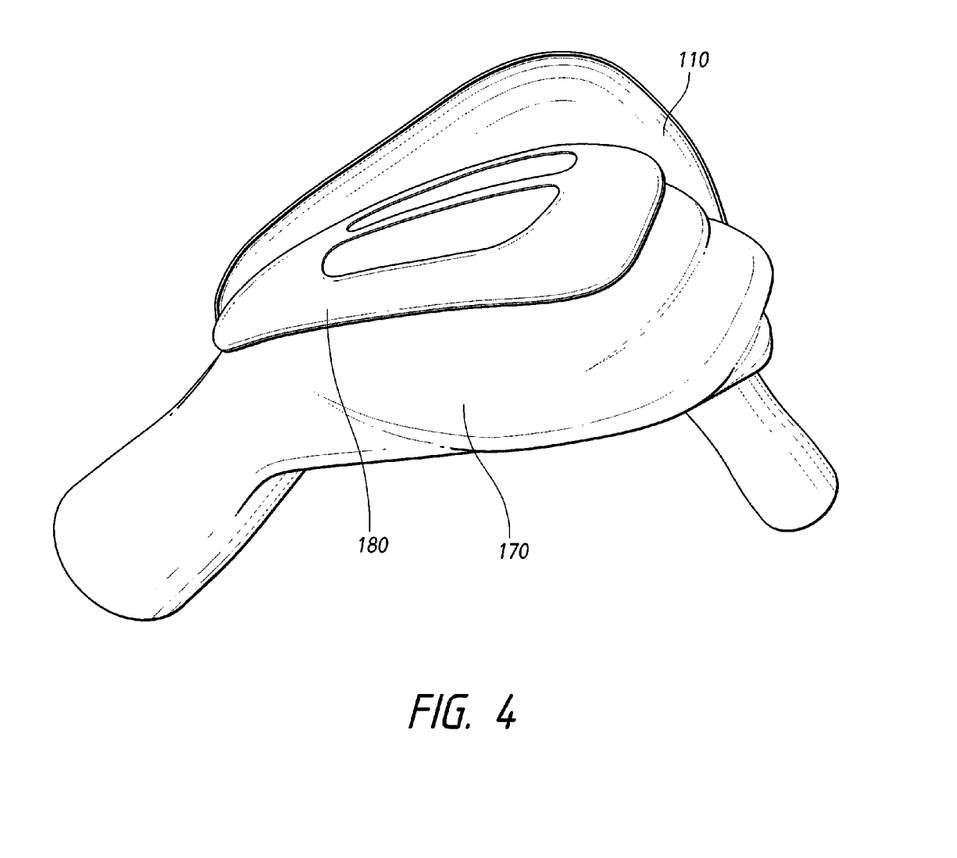
FIG. 4 is a plan view of the interior of a pediatric version of the artificial ventricle of the present invention.

FIG. 4 is a plan view of the interior of a pediatric version of the artificial ventricle of the present invention. Contractile element 180 is located on the exterior surface of compliance chamber 170, which is located within artificial ventricle housing 110. Inlet valve 120 (not shown) and outlet valve 130 (not shown) are located at opposite ends of artificial ventricle housing 110.

Figure 5:
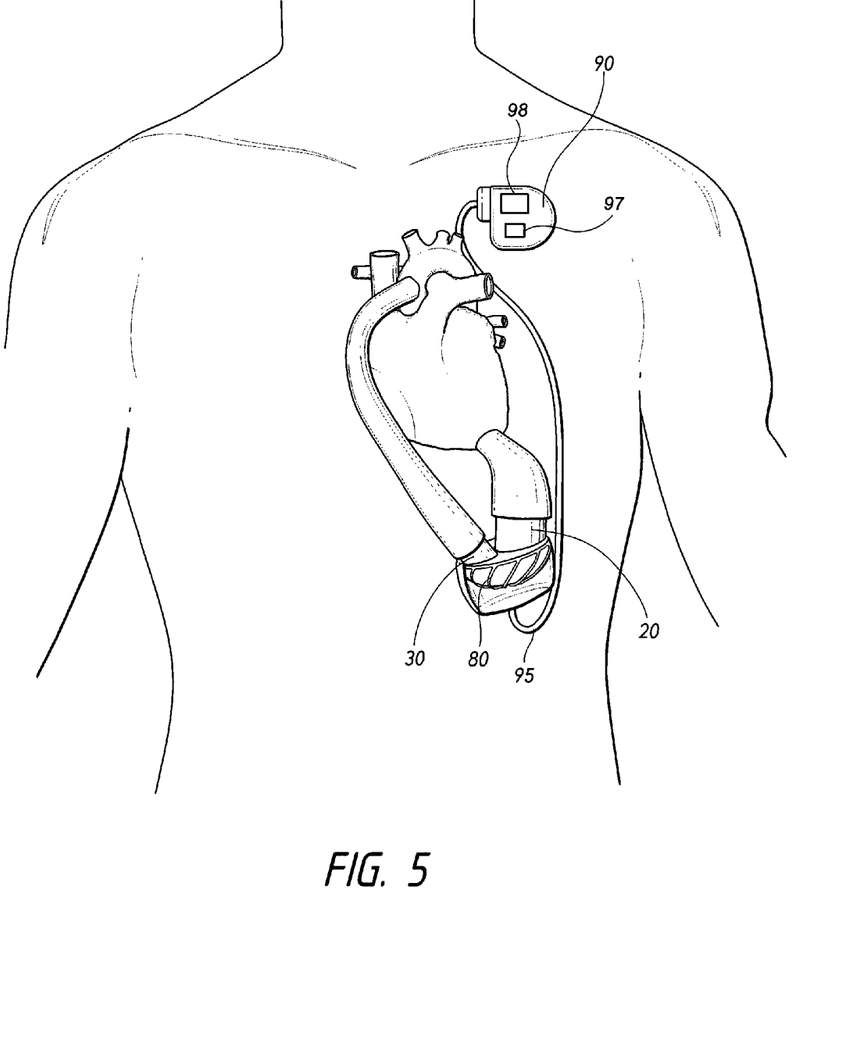
FIG. 5 is a plan view of the artificial ventricle implanted within a patient.

FIG. 5 is a plan view of the artificial ventricle of FIGS. 1-3 implanted within a patient. As illustrated therein, inlet 20 is connected to the patient's left ventricular apex and outlet 30 is anastomosed to the patient's aorta. Electrical energy source 90 is connected to contractile elements 80 via common electrode 95, and includes voltage regulator 97 and pacemaker 98.

Figure 6:
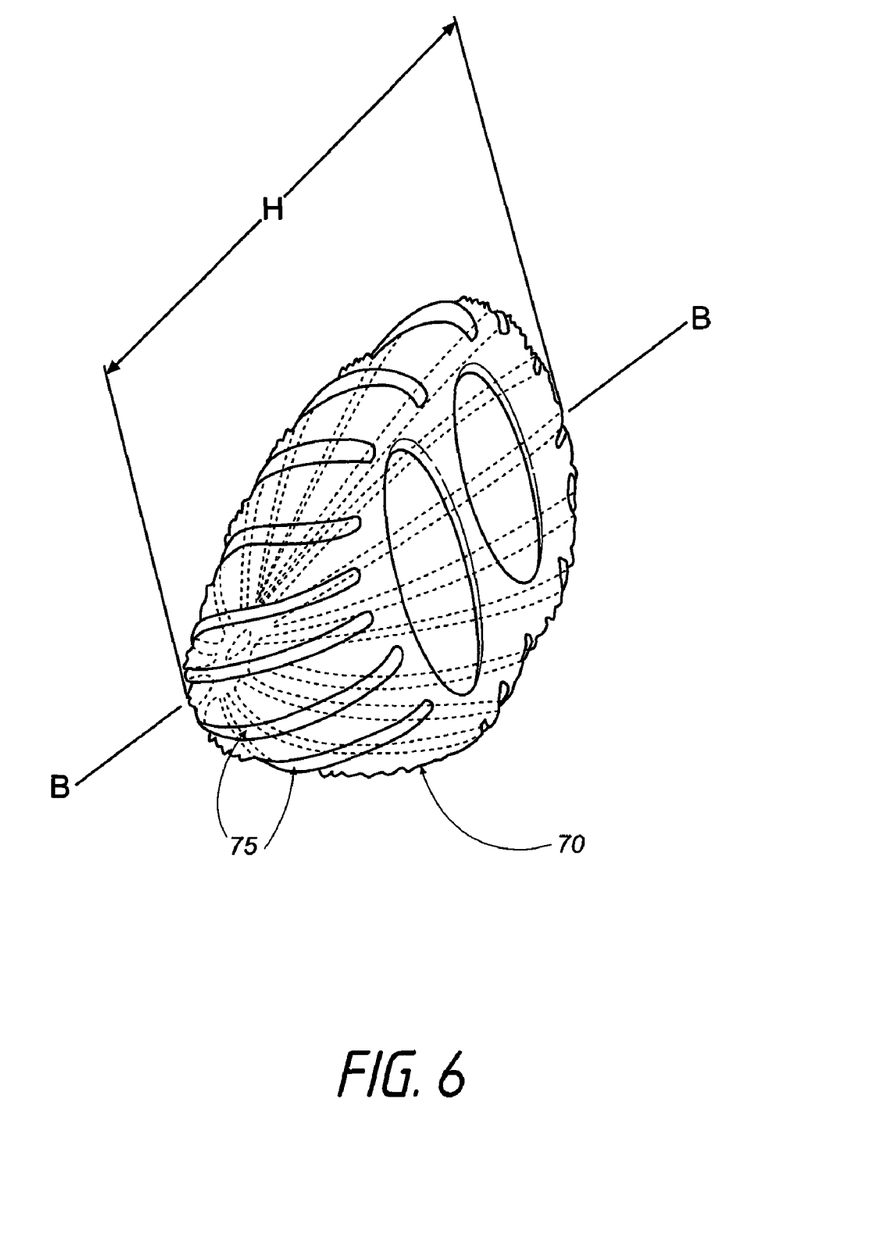
FIG. 6 is a plan view of a compliance chamber illustrating ridges arranged helically about the chamber's longitudinal axis B-B.

FIG. 6 illustrates a compliance chamber 70 having a plurality of ridges 75 arranged helically about the chamber's longitudinal axis B-B. The ridges facilitate placement of contractile elements (not shown) and to minimize or eliminate slippage of contractile elements during artificial ventricle operation.

The artificial ventricle and electrical energy device may be implanted without causing any interference with any function of any of the patient's organs. As illustrated in FIG. 5, the artificial ventricle may be preferably implanted within the patient's chest cavity, specifically the pericardial and pleural cavities. The electrical energy source may be conveniently located in the anterior chest wall, or abdominal wall but outside the chest cavity but still under the patient's skin.

The artificial ventricle of the present invention provides a new pulsatile, positive displacement mechanical circulatory support or replacement for one or both ventricles which is completely implantable with no external components. Additional advantages include a minimal hemolysis risk; minimal energy requirement and an extended service life on internal power supply.

The artificial ventricle of the present invention does not require an external battery pack or drive, vent lines or control cables traversing the skin. Accordingly, the present invention provides a maximum degree of patient mobility and a significantly lower risk of infection.

I claim:

1. An artificial ventricle, comprising:
(A) a pulsatile, positive-displacement blood pump comprising a biologically inert housing containing:
a hollow, flexible compliance chamber,
an inlet valve for said compliance chamber, said inlet valve adapted to be operatively connected to a patient's ventricular apex or atrial wall,
an outlet valve for said compliance chamber, said outlet valve adapted to be operatively connected to the patient's aorta or pulmonary artery;
a plurality of contractile elements radiating outward from an apex of said compliance chamber, said contractile elements being incorporated in and/or in contact with at least a portion of an outer surface of said compliance chamber, said contractile elements comprising an electroactive dielectric elastomer or an ion exchange membrane metallic composite, said contractile elements operatively connected to a common electrode, and
(B) an implantable energy source operatively connected to said common electrode,
wherein said electroactive dielectric elastomer is a member of the group consisting of polyaniline elastomers, polysulfone elastomers, polyacetylene elastomers, polypyrrole elastomers, polyvinylidene difluoride elastomers, silicone elastomers, and acrylic elastomers.

2. The artificial ventricle of claim 1, wherein said inlet valve comprises a cylindrical channel in communication with said compliance chamber, said channel containing a one-way valve selected from the group consisting of a ball check valve, a Gott valve, and a tri-leaflet pericardial valve.

3. The artificial ventricle of claim 1, wherein said outlet valve comprises a cylindrical channel in communication with said compliance chamber, said channel containing a one-way valve selected from the group consisting of a ball check valve, a Gott valve, and a tri-leaflet pericardial valve.

4. The artificial ventricle of claim 1, wherein said inlet and outlet valves are located at a base of said housing, with said inlet and outlet valves arranged at an angle of 90 to 120° to one another.

5. The artificial ventricle of claim 1, wherein said compliance chamber is made of polyester fabric or polytetrafluoroethylene fabric.

6. The artificial ventricle of claim 5, wherein said polyester fabric or polytetrafluoroethylene fabric has external ridges helically arranged about a longitudinal axis of said compliance chamber.

7. The artificial ventricle of claim 5, wherein said polyester fabric comprises polyethylene terephthalate coated with collagen.

8. The artificial ventricle of claim 5, wherein said polyester or polytetrafluoroethylene polyester comprises knitted double velour fabric or woven double velour fabric.

9. The artificial ventricle of claim 1, wherein said compliance chamber has an internal volume of 20-80 ml.

10. The artificial ventricle of claim 9, wherein said compliance chamber has a height of 4-10 cm and a diameter of 4-8 cm.

11. The artificial ventricle of claim 1, wherein said compliance chamber has a shape of a dome.

12. The artificial ventricle of claim 1, wherein said compliance chamber has a curved cylindrical shape, with said inlet and outlet valves located at opposite ends of said compliance chamber.

13. The artificial ventricle of claim 1, wherein said contractile elements comprise an electroactive dielectric elastomer, and said electroactive dielectric elastomer is an acrylic elastomer.

14. The artificial ventricle of claim 1, wherein said contractile elements comprise an ion exchange membrane metallic composite, and said ion exchange membrane metallic composite comprises perfluorocarboxylate-gold or sulfonated poly(styrene-ethylene-butylene-styrene).

15. The artificial ventricle of claim 1, wherein two or more of said contractile elements are inter-connected at a point other than said apex.

16. The artificial ventricle of claim 1, wherein said contractile elements are arranged helically.

17. The artificial ventricle of claim 1, further comprising additional contractile elements arranged circumferentially around a base of said compliance chamber.

18. The artificial ventricle of claim 1, wherein said housing has the shape of a truncated dome.

19. The artificial ventricle of claim 1, wherein said housing is made of titanium or polyurethane.

20. The artificial ventricle of claim 1, further comprising a common voltage regulator operatively connected between said electrode and said plurality of contractile elements.

21. The artificial ventricle of claim 1, wherein said implantable energy source comprises a pacemaker.

22. The artificial ventricle of claim 1, wherein said contractile elements are in elongated or strip form.

* * * * *